(12) United States Patent
Tawfik et al.

(10) Patent No.: US 10,112,773 B2
(45) Date of Patent: Oct. 30, 2018

(54) SYSTEM AND METHODS FOR ARCHIVING AND RETRIEVING SPECIMENS

(71) Applicant: University of Kansas, Lawrence, KS (US)

(72) Inventors: Ossama Tawfik, Leawood, KS (US); Swaran K. Jain, Lansing, KS (US); Terry N. Faddis, Lawrence, KS (US); Gavin Patrick Strunk, Wichita, KS (US)

(73) Assignee: University of Kansas, Lawrence, KS (US)

( * ) Notice: Subject to any disclaimer, the term of this patent is extended or adjusted under 35 U.S.C. 154(b) by 0 days.

(21) Appl. No.: 15/457,248

(22) Filed: Mar. 13, 2017

(65) Prior Publication Data

US 2017/0327313 A1 Nov. 16, 2017

Related U.S. Application Data

(63) Continuation of application No. 14/420,609, filed as application No. PCT/US2013/054330 on Aug. 9, 2013, now abandoned.

(60) Provisional application No. 61/681,483, filed on Aug. 9, 2012.

(51) Int. Cl.
*B65G 1/137* (2006.01)

(52) U.S. Cl.
CPC ........ *B65G 1/1371* (2013.01); *B65G 2209/04* (2013.01)

(58) Field of Classification Search
USPC ........................................................ 700/218
See application file for complete search history.

(56) References Cited

U.S. PATENT DOCUMENTS

| | | | | |
|---|---|---|---|---|
| 5,226,782 A | * | 7/1993 | Rigling | B65G 1/0407 198/347.3 |
| 2004/0009098 A1 | | 1/2004 | Torre-Bueno | |
| 2008/0188977 A1 | * | 8/2008 | Palmer | A23B 4/06 700/215 |

(Continued)

FOREIGN PATENT DOCUMENTS

| WO | WO 2012/037482 | 3/2012 |
|---|---|---|
| WO | WO 2014/026107 | 2/2014 |

OTHER PUBLICATIONS

Johnston et al. Optimized Pathology Sample Storage System. Dec. 11, 2007 [retrieved on Dec. 30, 2013]. Retrieved from the Internet. <URL: http://deepblue.lib.umich.edu/bitstream/handle/2027.42157951/?sequence=I >.

(Continued)

*Primary Examiner* — Kyle O Logan
(74) *Attorney, Agent, or Firm* — Ray Quinney & Nebeker P.C.; Paul N. Taylor

(57) ABSTRACT

Embodiments of the present invention include a system and methods for archiving and/or retrieving specimens. Embodiments of the system of the present invention include a movement mechanism, an archival structure, and a software program. Embodiments of the device are configured to acquire a specimen, transport the specimen to a unique location in the archival structure, and store information regarding specimen identification and storage location.

20 Claims, 10 Drawing Sheets

(56) References Cited

U.S. PATENT DOCUMENTS

| | | | |
|---|---|---|---|
| 2012/0163680 A1* | 6/2012 | Lefebvre | G01N 1/312 382/128 |
| 2013/0236276 A1* | 9/2013 | Richter | B01L 3/00 414/222.07 |
| 2015/0217936 A1 | 8/2015 | Tawfik et al. | |

OTHER PUBLICATIONS

U.S. Appl. No. 14/420,609, Sep. 14, 2016, Office Action.

* cited by examiner

SYSTEM AND METHODS FOR ARCHIVING AND RETRIEVING SPECIMENS

CROSS-REFERENCE TO RELATED APPLICATION

This patent application claims the benefit of U.S. Provisional Patent Application No. 61/681,483, filed on Aug. 9, 2012, and which is hereby incorporated by reference in its entirety.

FIELD OF THE INVENTION

The invention relates generally to an automated system and methods for archiving and retrieving specimens that may be used by practitioners to conduct analyses, make determinations, diagnose conditions, render conclusions, and provide assistance or treatment. Examples of such specimens include those used by health care providers—such as histology slides and tissue cassettes, those used in petroleum exploration—such as material taken from core samples or other geological materials, and those used by arborists, botanists, or agricultural specialists—such as samples of plant tissue.

BACKGROUND OF THE INVENTION

A variety of practitioners prepare and examine specimens to obtain useful information. Those involved in petroleum or other geological exploration often prepare specimens from core samples or rock samples in order to determine whether a site may be of commercial value. Those involved in agriculture or horticulture often must prepare specimens of plants or trees to determine the identity or condition of the subject. Those involved in medicine often must archive and retrieve specimens of a patient's cells or tissues in order to diagnosis and treat a patient. Those involved in investigations often must archive and retrieve specimens of cells or tissue from a subject to identify a person for purposes of criminal investigation, criminal prosecution, paternity testing, genetic testing, or other. Although the present invention is discussed in this application with reference to histological specimens, such as those generally stored in slides or tissue cassettes, the present invention also includes embodiments of systems and methods for archiving and retrieving specimens including soil specimens, geology specimens, plant specimens, food specimens, hydrology specimens, archeological specimens, zoology specimens, criminal evidence specimens, or any other specimen.

Regarding conventional systems and methods for archiving and retrieving specimens, it is well known to store specimens of cells or tissues in a container such as a slide, cassette, block, petri dish, vial, bottle, or other storage containers. In order to do so, specimens must be sized and shaped to fit in the conventional slide or cassette container. In other embodiments, the specimens are stored on or in a container having a size and shape other than a conventional slide or cassette, or are not stored in a container at all. For purposes of this application, the term "specimen" will be used generally to refer to a specimen alone, a specimen treated with a fixing agent, or a specimen in combination with the container in which it is stored. A specimen in combination with a container in which or on which it is stored is also termed a "container specimen" for purposes of this application.

After they are prepared, specimens are often sent to a laboratory or other facility for processing, analysis, or storage. Such laboratories typically handle a large number of specimens. Currently, many laboratories employ the same techniques to store and retrieve specimens that they have been using for many years. In some cases, laboratory employees must move large numbers of specimens at any given time back and forth from extensive storage areas.

With respect to storage, certain conventional systems and procedures require a person to manually place each specimen on a tray, to stack the trays while specimens are processing, to categorize specimens after processing, to move the categorized specimens to a second location for long-term storage, and to prepare a record of where the specimen is stored. Other conventional systems require an additional step of the positioning of specimens in a specific orientation for processing and then returning such specimens to a tray.

With respect to retrieval, conventional systems and methods require a person to look up the location in which a specimen is stored in the relevant records, go to the location, match the physical location with the recorded location, pull out specimen, and record the specimen as "checked out" or removed. Such retrieval steps may be conducted on multiple occasions that a specimen may need to be retrieved.

Clearly, existing systems and procedures are labor intensive, tedious, time-consuming, inefficient, and error-prone. Such systems and procedures often require the full attention of a laboratory technician. In addition, a specimen cannot be easily located at certain times during the course of the procedure since a record of interim locations is often not made. Also, the time-consuming steps delay the diagnosis or treatment of a patient.

Other disadvantages of existing systems and methods include the possibility for loss, damage, or mismanagement of specimens, which may have serious consequences to patient care, criminal prosecutions, and research objectives. Because of the seriousness of the consequences, there may be liability issues such as malpractice or privacy concerns with mishandling of specimens.

Attempts to improve the known systems and methods to facilitate the storage and retrieval of specimens have been made. However, often these systems and methods require the use of complex apparatus, for example, to treat slides such as by staining specimens on slides, to wash specimens on slides, to position coverslips on slides, or to make digital images of the specimens. Such inefficient apparatus use space that could be used to store additional specimens, and accordingly, do not maximize the number of specimens that could be stored in that space.

Also, certain conventional methods call for the discarding of specimens in order to resolve storage space issues. The College of American Pathologists has recognized the problem of storing specimens for long periods of time and has lowered its standards to permit discarding certain types of specimens earlier. However, such methods of discarding specimens earlier may have a detrimental impact on patient care, research, and criminal investigations.

Conventional systems and methods are often expensive to implement and maintain. As an example, certain hospitals may generate around one million specimens per year. Since workplace regulations often limit the height of certain types of storage bureaus, additional building square footage is often required to provide sufficient storage space for specimens.

Accordingly, there is a need for a system and methods for archiving and retrieving a collection of specimens that utilize automated elements which permit archiving and retrieving with improved efficiency, decreased cost, and in which space for the storage of specimens is maximized.

SUMMARY OF THE INVENTION

Embodiments of the present invention include a system and methods for archiving and/or retrieving specimens. Embodiments of the system of the present invention include a movement mechanism, an archival structure, and software program. Certain embodiments of the present invention are configured to archive and retrieve specimens stored in a plethora of generally identically sized containers. Other embodiments are configured to archive and retrieve containers of varying sizes.

Embodiments of a movement mechanism are configured to acquire a specimen, transport the specimen to a unique location in the archival structure, retrieve the specimen from the archival structure, and position the specimen for user access. The movement mechanism also may be configured to send information to and receive information from the software program. The movement mechanism may include a reader configured to read a specimen information display, such as a UPC barcode, matrix barcode, QR code, or other, which may be associated with the specimen.

The movement mechanism may be controlled through a user-friendly software program executable through a computer system. The software program may be configured to permit receiving, storing, and accessing information related to each specimen for ease of tracking and subsequent retrieval of the specimen. Specifically, the software program may assign and record the unique location of the specimen when positioned in the archival structure.

Embodiments of the archival structure may include receptacles configured to receive specimens. Certain receptacles may be sized and shaped to receive specific types of specimens, for example, slides or cassettes. Each receptacle is associated with a unique location identifier and may include a receptacle information display configured to be readable by a reader.

The system and methods obviate the need for manual storage and retrieval of histology specimens. Advantageously, users can quickly process, store, retrieve, and or analyze specimens, while reducing the likelihood of error, loss, or breakage of slides and/or tissue cassettes. Automation of the storage and retrieval process also will save time, money, and effort. Additionally, accuracy and efficiency will be improved. Also, liability for lost or broken specimens may be avoided.

Another advantage of embodiments of the present invention includes maximizing storage space for specimens, which decreases storage cost. Embodiments of the present invention may be able to store, for example, slides and cassettes collected in 20 years in a space of specimens collected in 1 year in a conventional apparatus.

The present invention and its attributes and advantages may be further understood and appreciated with reference to the detailed description below of contemplated embodiments, taken in conjunction with the accompanying drawings.

DETAILED DESCRIPTION

Figure 1:
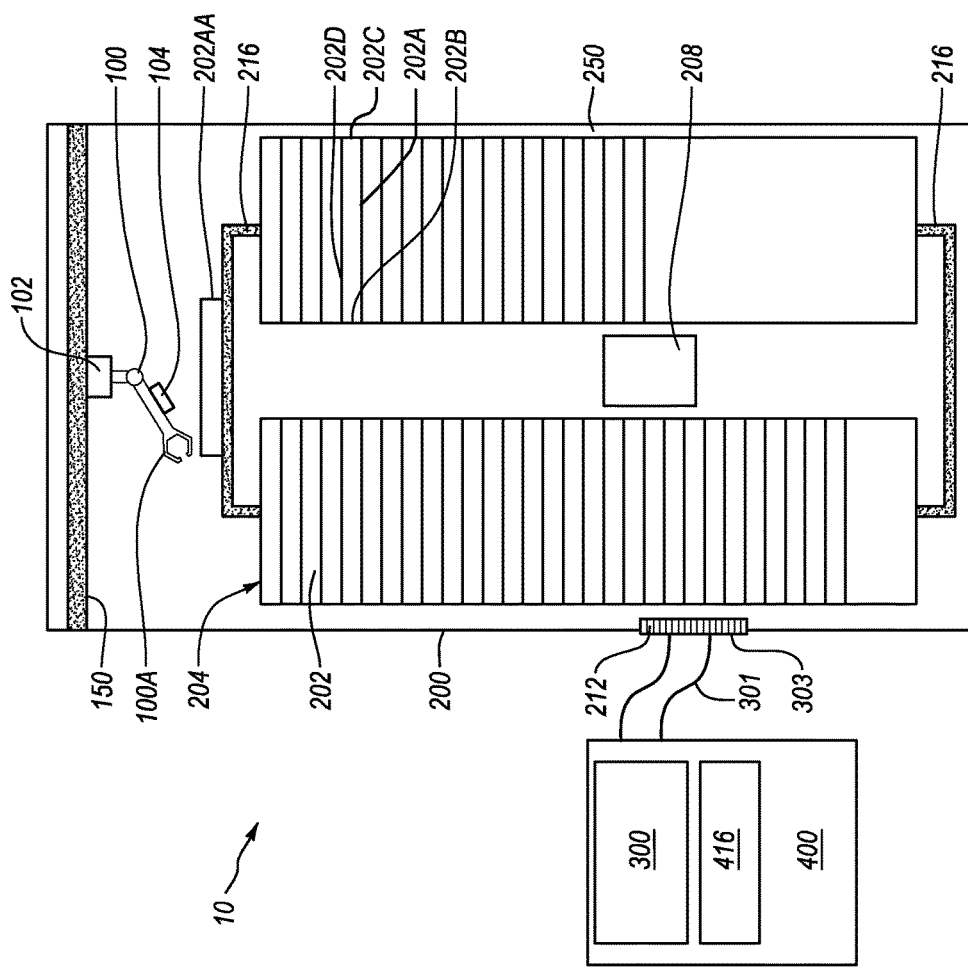
FIG. 1 is a front view of an embodiment of the system according to the present invention.

Embodiments of the systems and methods for archiving and retrieving specimens may be configured for use in an anatomical pathology laboratory, a criminal forensics laboratory, research laboratory, or other setting. Certain embodiments of the system 10 include a movement mechanism 100, an archival structure 200 including receptacles 202 in which specimens may be archived, and a software program 300 executable on a computer system 400. Certain embodiments of the movement mechanism 100 and the archival structure 200 may be positioned within a housing 250.

As illustrated in FIG. 1, certain embodiments of the movement mechanism 100 are configured as a robotic arm 100A, but certain embodiments include a robotic arm and gripper or just a robotic gripper. For example, the gripper may include two or more generally opposing members that may actuate from an open position, where the members are spaced apart from each other, toward and/or to a closed position, where the members are touching each other. When acquiring or retrieving a specimen, the gripper may not reach the closed position, as the specimen will be located between the members. In other embodiments, the gripper may not grip the specimen, but rather, may simply lift the specimen and carry it upon a base member. In further embodiments, the gripper may include a magnet or other engaging member that may facilitate acquisition and/or retrieval of the specimen. For example, the gripper may include an electromagnet that may engage a ferromagnetic, or partially ferromagnetic, material connected to the specimen when the electromagnet is turned on and may release the specimen when the electromagnet is turned off. In a still further embodiment, the gripper may engage with the specimen using a snap fit, or other mechanical interface that may facilitate engagement and disengagement. In other embodiments, the gripper and/or other portions of the robotic arm 100A may include suction cups or servos and suction cups. The robotic arm 100A may be connected at one or more points to a base element 150. The base element 150 may be configured to be mobile so as to position the robotic arm 100A closer to the receptacles. Other embodiments of the base element 150 are generally not intended to be mobile during the course of use of the system.

Embodiments of the movement mechanism 100 may be configured to acquire and move only specimens having one specific size and shape. For example, in one embodiment, all of the specimens may be of generally a single size and shape, i.e. a standard microscope slide or tissue cassette. Other embodiments of the movement mechanism are configured to acquire and move any of a group of specimens having a narrow range of sizes, shapes, weights, or combinations thereof. For example, a narrow range of sizes and shapes may include a difference in size in a range of from about 0.001 inches to about 1.000 inches. In other examples, the difference in size may be more than about 1.000 inches. The difference in size may be the difference in overall volume, difference in a measurement of length (i.e. height, width, thickness, diagonal etc.), difference in perimeter (i.e. circumference or other measures of perimeter), difference surface area, differences in other measurements, or combinations thereof. Narrow ranges in shape may include differences in internal angles, differences in curvature, other shape differences, or combinations thereof. Narrow ranges in weights may include differences on the order of about 1 microgram, 1 gram, 10 grams, 100 grams, 1 kg, 5 kg, etc. Specimen weights may range from less than about 10 grams, more than about 1 kg, between about 1 grams and about 15 grams, or other ranges in weight. The sizes, shapes, or weights may be measured based on the specimen alone or may be measured based on the specimen and the receptacle. Still other embodiments are configured to handle specimens having a wide range of sizes, shapes, weights, or combinations thereof.

As illustrated in FIG. 1, embodiments of an archival structure 200 include receptacles 202 configured to receive and store specimens. A receptacle 202 may include a bottom receptacle wall 202A, a first side receptacle wall 202B, a second side receptacle wall 202C, and a top receptacle wall 202D. Other embodiments include only a bottom receptacle wall 202A. Two or more receptacles 202 may be positioned relative to one another in groups such as modules 204 that form columns, rows, clusters, or other groupings. The receptacles 202 may be stacked or interconnected in such modules 204.

Embodiments of the archival structure 200 may also include an input component 208 configured to permit a user to insert the specimen or a group of specimens that are ready for archival. In some embodiments, the input component 208 also may be the output location in which the movement mechanism 100 places the specimen after retrieval to permit the user to remove that specimen from the system 10. In some embodiments there are one or multiple input/output components 208. In other embodiments, one or multiple input components may be separate from one or multiple output components.

Certain embodiments of a system 10 and methods are configured to archive high volumes of specimens, such as hundreds of specimens, thousands of specimens, or millions of specimens. Such embodiments may include one or more input/output components 208. Such embodiments also may include more than one movement mechanism 100, and each movement mechanism 100 may be positioned and configured to position specimens in and retrieve specimens from a module 204 of receptacles 202.

Archival structure 200 may position the specimens in the order of insertion into the input/output component 208, by size, by weight, by shape, or randomly. For example, the first specimen inserted into the archival structure 200 is positioned in a first position while the second specimen inserted into the archival structure 200 is positioned in a second position, et cetera. In another example, the specimens may be grouped according to size, i.e. larger specimens may be grouped with larger specimens while smaller specimens may be grouped with smaller specimens. In a further example, specimens of a particular shape, i.e. a cylindrical shape, may be grouped with specimens of a similar shape while specimens of another shape, i.e. a prismatic shape, may be grouped with specimens of the other shape, i.e. prismatic shape. Also, an archival structure 200 may be configured to prioritize placement of specimens automatically according to user requirements, for example, upon entry by user of certain instructions. A user may plan to access specimen after a short period of time, and provide instructions to the archival structure 200 accordingly. In response, the archival structure 200 may provide short-term storage, which may include one or more receptacles positioned relatively close to the input/output component 208 such that the specimen may be retrieved faster and more easily. In another embodiment, the placement of the specimens may be automatically determined by the computer system 400. For example, the placement of the specimens may be automatically determined based on the number of times each specimen is retrieved. In another example, the placement may be automatically determined based on estimated demand for similar specimens. For instance, certain types of histology specimens may be in high demand for a short period of time, but after that period of time may no longer be in demand. Thus, after the initial high demand period of time, the specimens that are no longer in high demand may be positioned in a location that may allow specimens that are currently in high demand to be in a more quickly accessible position (i.e. low demand specimens may be positioned further away from the input/output 208 than the higher demand specimens). Other short-term storage may be in receptacles 202 configured to be movable, as opposed to certain other receptacles 202 which are generally not intended to be movable during the course of use of the system.

A user also may plan to not access a specimen for a long period of time, and provide those instructions to the archival structure 200 accordingly. In response, the archival structure 200 may provide long-term storage, which may include one or more receptacles 202 relatively further from the input/output component such that closer receptacles are reserved for often-accessed specimens. Other long-term storage may be provided in receptacles 202 configured not to be movable during the course of use of the system—that is, "non-movable" receptacles. Certain embodiments of the present invention may include only movable receptacles, only generally non-movable receptacles, or a combination of movable and non-movable receptacles.

The embodiment illustrated in FIG. 1 includes certain receptacles 202 configured to be movable. Each receptacle 202 may be movable to a position easily accessible by a movement mechanism 100. Receptacle 202AA is shown in such a position. Receptacles 202 may be moved individually or may be moved as a group such as when an entire module 204 moves all at once. In some embodiments, the receptacles may be moved, handled, or arranged using an air cylinder system or system of air cylinders. In other embodiments, the receptacles may be moved, handled, or arranged using suction cups that may additionally be configured to operate with servos. In further embodiments, the receptacles may be moved, handled, or arranged using suction cups that may additionally be configured to operate with a power screw.

Figure 2:
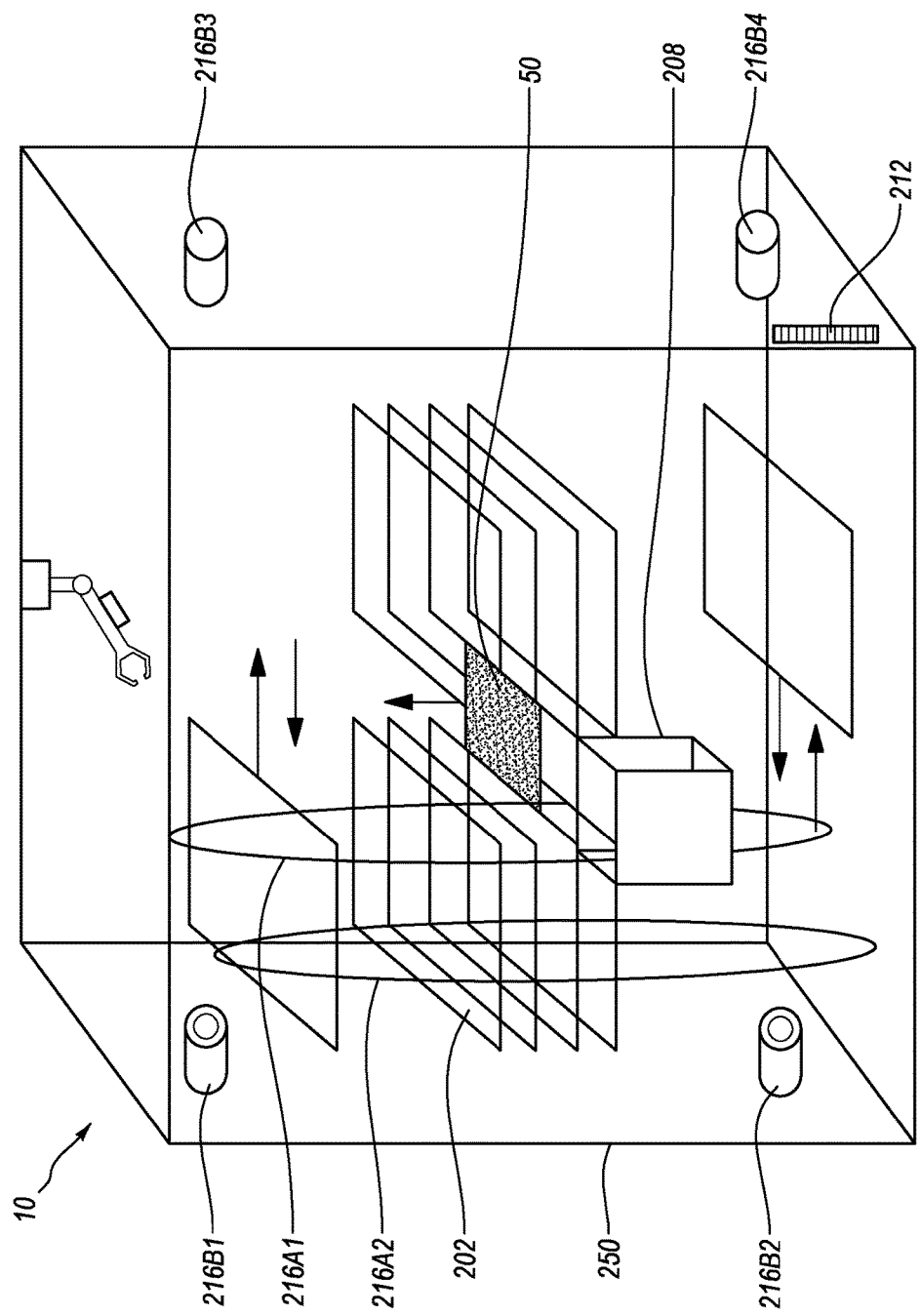
FIG. 2 is a perspective view of an embodiment of the system according to the present invention.

FIG. 2 illustrates a specimen 50 and an embodiment of the archival structure 200 including a number of receptacles 202, an input/output component 208, and a housing 250. The embodiment shown in FIG. 2 may include elements of the embodiment of FIG. 1 and therefore, the description of FIG. 1 is hereby incorporated by reference. The archival structure 200 also includes receptacle positioning components 216 configured to move or position the receptacles 202. Certain embodiments include two types of receptacle positioning components 216, such as a vertical receptacle positioning component 216A configured to control the vertical position of a receptacle and a horizontal receptacle positioning component 216B configured to control the generally horizontal position of a receptacle. Receptacle positioning components 216 may include, for example, an air cylinder with a pusher rod or plurality of air cylinders and pusher rods, suction cups, servos with suction cups, a power screw or plurality of power screws, or any combination thereof. The illustrated embodiment in FIG. 2 includes a first vertical receptacle positioning component 216A1, a second vertical receptacle positioning component 216A2, first horizontal receptacle positioning component 216B1, and a second horizontal receptacle positioning component 216B2. In certain embodiments, a positioning component 216 rotates in multiple orientations such that only one positioning component 216 can position receptacles vertically and horizontally.

Figure 3:
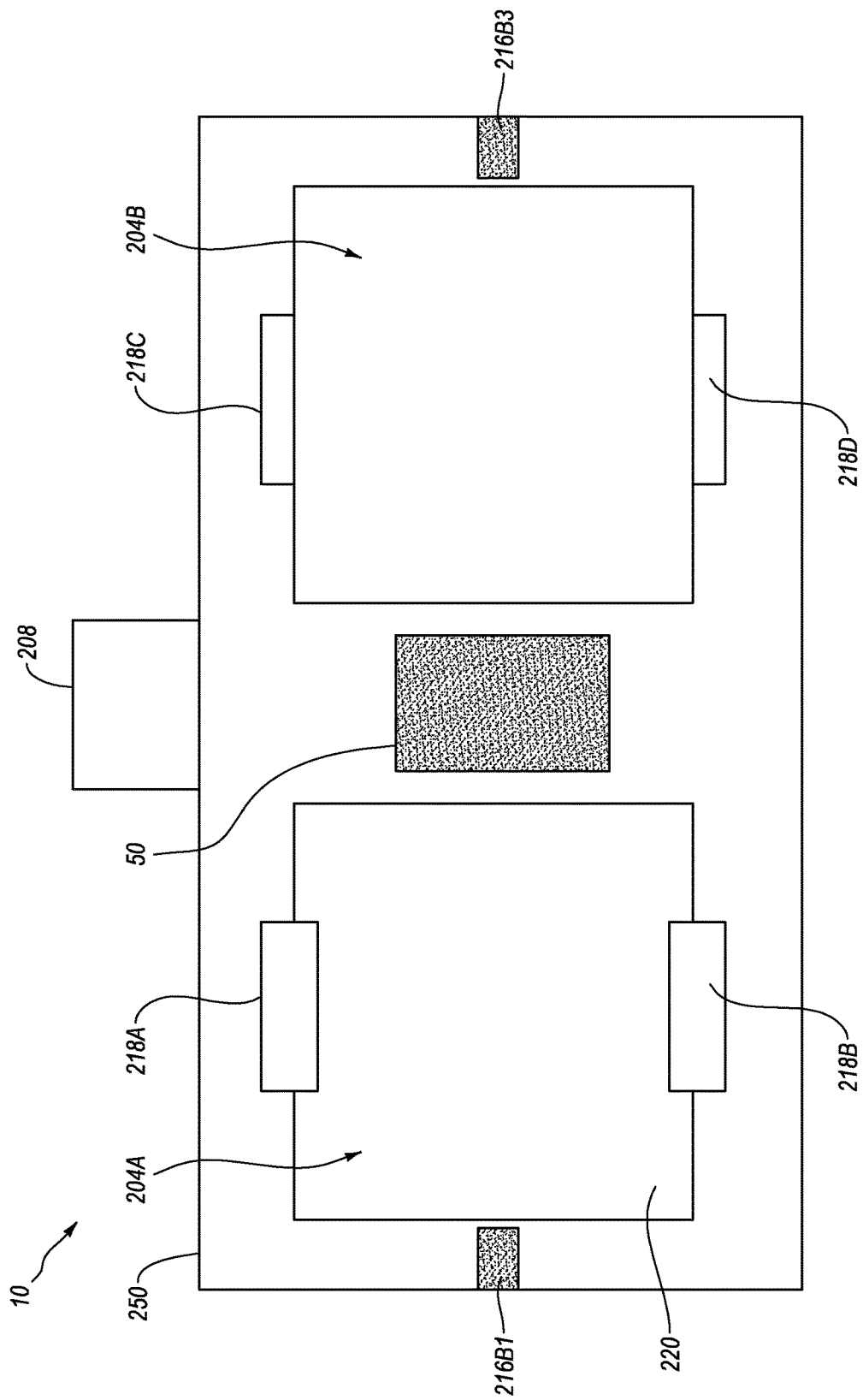
FIG. 3 is a top view of an embodiment of the system according to the present invention.

FIG. 3 illustrates a specimen 50 and a system embodiment including a first module 204A of receptacles 202, a second module of receptacles 204B, an input/output component 208, and a housing 250. The embodiment shown in FIG. 3 may include elements of the embodiments of FIGS. 1 and 2 and therefore, the description of FIGS. 1 and 2 are hereby incorporated by reference. In the embodiment illustrated in FIG. 3, the receptacles 202 are formed from a series of support element pairs 218 and plate elements 220. Each support element pair 218 is configured to support a plate element 220 on which a specimen 50 may be positioned. Other support element pairs 218 are configured to support a specimen 50 directly. Certain embodiments of support elements 218 may be mounted on a receptacle positioning component 216, on the housing 250, or a support element scaffold.

Certain embodiments of the plate element 220 are fixedly attached to the support element 218 such that the plate element 220 is configured to remain permanently attached to the support elements 218. Other embodiments of a plate element 220 are configured to meet with or removably attach to the support elements 218.

In certain embodiments, the plate element 220 may be supported by support elements 218 that connect to one another to form a continuous bottom receptacle wall 202A. In other embodiments, each support element 218 is not in direct contact with each other support element 218. Embodiments of each support element pair 218 may include a first support element 218A, 218C and a second support element 218B, 218D positioned generally in the same plane relative to one another to permit positioning of a plate element 220, as illustrated in FIG. 3. Other embodiments include only one support element 218 per receptacle, or three or more support elements 218 per receptacle.

Embodiments of a plate element 220 may include a bottom surface and a top surface. The bottom surface may be configured to meet with and be supported by a support element pair 218. Also, when receptacles 202 are stacked, such as positioned generally above and below the other, the bottom surface of a plate element 220 may form a top receptacle wall 202D relative to a lower receptacle. A top surface of the plate element 220 may form the bottom receptacle wall 202A relative to an upper receptacle. The top surface of a plate element 220 also may be configured to receive one or more specimens. Such receiving section of a plate element 220 may include a generally flat portion, a generally concave portion, or a receiving section configured to receive a specimen of a specific size and shape.

In certain embodiments, the receptacles 202 are configured to maximize the storage space and permit storage of many, many specimens. The space required for storing a single specimen may be the volume of the specimen plus fifty percent. The additional fifty percent may be attributed to storage space for various mechanisms of the system. In certain embodiments in which a specimen includes a slide, each specimen may require approximately 0.0005 cubic feet of storage. For example, 400,000 slides may require 200 cubic feet, which is equivalent to a cube with 5.848 feet sides. In embodiments in which a specimen includes a cassette, each cassette may require approximately 0.000625 cubic feet of storage. For example, 400,000 cassettes would require 250 cubic feet, which is equivalent to a cube with 6.299 feet sides.

Referring back to FIG. 1, it also illustrates the software program 300 executable on a computer 400. Embodiments of the present invention may comprise or utilize a special-purpose or general-purpose computer system 400 that includes computer hardware, such as, for example, one or more processors 406 and system memory, as discussed in greater detail below. Embodiments within the scope of the present invention also include physical and other computer-readable media for carrying or storing computer-executable instructions and/or data structures. Such computer-readable media can be any available media that can be accessed by a general-purpose or special-purpose computer system 400. Computer-readable media that store computer-executable instructions and/or data structures are computer storage media. Computer-readable media that carry computer-executable instructions and/or data structures are transmission media. Thus, by way of example, and not limitation, embodiments of the invention can comprise at least two distinctly different kinds of computer-readable media: computer storage media and transmission media.

Computer storage media are physical storage media that store computer-executable instructions and/or data structures. Physical storage media include computer hardware, such as RAM, ROM, EEPROM, solid state drives ("SSDs"), flash memory, phase-change memory ("PCM"), optical disk storage, magnetic disk storage or other magnetic storage devices, or any other hardware storage device(s) which can be used to store program code in the form of computer-executable instructions or data structures, which can be accessed and executed by a general-purpose or special-purpose computer system to implement the disclosed functionality of the invention.

Transmission media can include a network and/or data links which can be used to carry program code in the form of computer-executable instructions or data structures, and which can be accessed by a general-purpose or special-purpose computer system. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer system, the computer system may view the connection as transmission media. Combinations of the above should also be included within the scope of computer-readable media.

Information may be transferred between the archival structure and the software program 300 and the computer 400 through transmission media such as communication interface 301. The communication interface 301 may include a computer communication interface 416 and a device communication interface 303, such as a movement mechanism communication interface 102 or an archival structure communication interface 212. The communication interface 301 allows software, instructions, and data to be transferred between the computer system 400 and external devices including the movement mechanism 100, the archival structure 200, or other components of the system 10. Software, instructions, and/or data transferred by the communication interface 301 are typically in the form of signals that may be electronic, electromagnetic, optical, or other signals capable of being sent and received by the computer communication interface 416 and the receiving communication interface 303. Signals may be sent and received using a network and/or data links which can be used to carry program code in the form of computer-executable instructions or data structures (either hardwired, wireless, or a combination of hardwired or wireless). For example, computer-executable instructions may be sent and received using a wire or cable, fiber optics, a phone line, a cellular phone link, a Radio Frequency ("RF") link, wireless link, or other communication channels.

Embodiments of the software program 300 may include a user interface through which a user may enter directions that will be sent to the movement mechanism 100, archival structure 200, or other components of the system 10. The software program 300 is configured to store information regarding the location of the specimens and information regarding other components of the system 10 in, for example, computer storage media.

Figure 4:
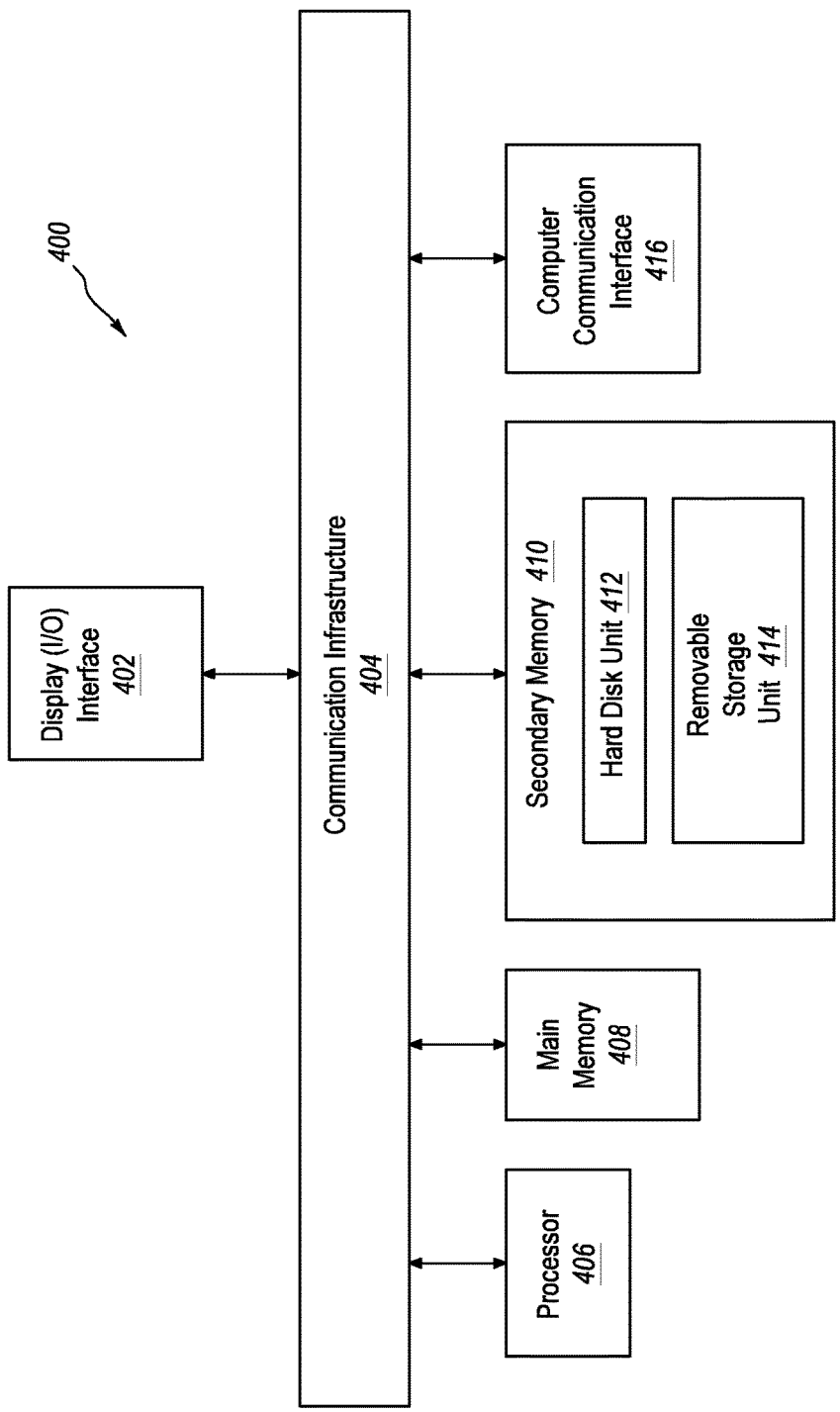
FIG. 4 illustrates an embodiment of a computer system on which the software program may run.

FIG. 4 illustrates an embodiment of a computer system 400 that may be used to implement the methods described herein. One or more computer systems 400 may carry out the methods presented in this application as computer executable instructions.

Computer system 400 may include a user interface 402 connected to communication infrastructure 404—such as a bus—which is used to forward data such as graphics, text, and information, from the communication infrastructure 404 or from a frame buffer (not shown) to other components of the computer system 400. The user interface 402 may permit a user to enter information or instructions and view feedback or information displayed through the software 300. The user interface 402 may include, for example, a keyboard, touch screen, joystick, trackball, mouse, monitor, speaker, printer, any other computer peripheral device, or any combination thereof, capable of entering and/or receiving or viewing data.

The embodiment shown in FIG. 4 may comprise or utilize a special-purpose or general-purpose computer system 400 that includes computer hardware, such as, for example, one or more processors 406 and system main memory 408, which may include, for example physical storage media such as RAM, ROM, EEPROM, solid state drives ("SSDs"), flash memory, phase-change memory ("PCM"), optical disk storage, magnetic disk storage or other magnetic storage devices, or any other hardware storage device(s) or combination thereof which can be used to store program code in the form of computer-executable instructions or data structures, which can be accessed and executed by a general-purpose or special-purpose computer system to implement the disclosed functionality of the invention. Computer system 400 may also include a secondary memory 410 such as a hard disk unit 412, a removable storage unit 414, or any combination thereof. Computer system 400 may also include transmission media such as a computer communication interface 416, for example, a modem, a network interface (such as an Ethernet card or Ethernet cable), a communication port, a PCMCIA slot and card, wired or wireless systems (such as Wi-Fi, Bluetooth, Infrared), local area networks, wide area networks, intranets, or other components capable of permitting communication between the software program 300 and other components of the system 10.

It is contemplated that the main memory 408, secondary memory 410, computer communication interface 416, or a combination thereof, function as a computer usable storage medium, otherwise referred to as a computer readable storage medium, to store and/or access computer software including computer instructions. For example, computer programs or other instructions may be loaded into the computer system 400 such as through a removable storage device, for example, a floppy disk, ZIP disks, magnetic tape, portable flash drive, optical disk such as a CD or DVD or Blu-ray, Micro-Electro-Mechanical Systems ("MEMS"), nanotechnological apparatus. Specifically, computer software including computer-executable instructions may be transferred from the removable storage unit 414 or hard disc unit 412 to the secondary memory 410 or through the communication infrastructure 404 to the main memory 408 of the computer system 400. For example, upon reaching various computer system components, program code in the form of computer-executable instructions or data structures can be transferred automatically from transmission media to computer storage media (or vice versa). For example, computer-executable instructions or data structures received over a network or data link can be buffered in RAM within a network interface module (e.g., a "NIC"), and then eventually transferred to computer system RAM and/or to less volatile computer storage media at a computer system. Thus, it should be understood that computer storage media can be included in computer system components that also (or even primarily) utilize transmission media.

Computer programs 300, when executed, enable the computer system 400, particularly the processor 406, to implement embodiments of the methods described herein according to computer software 300 including computer-executable instructions and data. The computer-executable instructions may be, for example, binaries, intermediate format instructions such as assembly language, or even source code.

The computer system 400 described in this application may perform any one of, or any combination of, the steps of any of the methods presented in this application. It is also contemplated that embodiments of the methods described herein may be performed automatically, or may be invoked by some form of manual intervention.

The computer system 400 of FIG. 4 is provided only for purposes of illustration, such that the invention is not limited to this specific embodiment. It is appreciated that a person skilled in the relevant art knows how to program and implement the invention using any computer system with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like. The invention may also be practiced in distributed system environments where local and remote computer systems, which are linked (either by hardwired data links, wireless data links, or by a combination of hardwired and wireless data links) through a network, both perform tasks. As such, in a distributed system environment, a computer system may include a plurality of constituent computer systems. In a distributed system environment, program modules may be located in both local and remote memory storage devices.

Certain embodiments of the software program 300 may be integrated with other automated systems within the laboratory or other environment in which it is implemented. For example, the software program 300 may be integrated with electronic medical records systems, digital microscopy, and/or digital scanning. Such embodiments may improve workflow, improve patient care because of reduced errors and delay in diagnosis, reduce cost due to increased efficiency, and improve morale.

Figure 5:
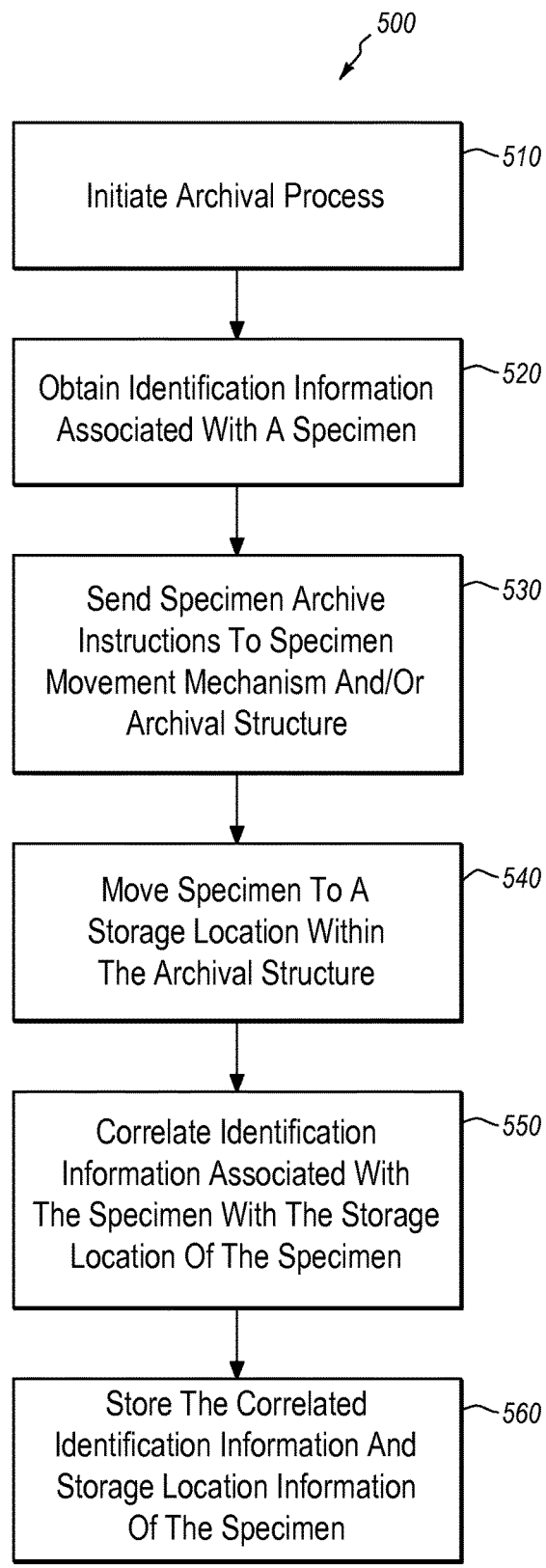
FIG. 5 illustrates an embodiment of a method for archiving specimens according to the present invention.

FIG. 5 illustrates an embodiment of an archival method 500 of archiving a specimen or a collection of specimens according to the present invention. In one embodiment of such a method, the archival process is initiated 510, identification information associated with a specimen is obtained 520, specimen archive instructions are sent to the movement mechanism and/or the archival structure 530, the specimen is moved to a storage location within the archival structure 540, identification information associated with the specimen is correlated to the storage location of the specimen 550, and the correlated identification information and storage location information is stored on a computer readable storage medium 560.

Figure 6:
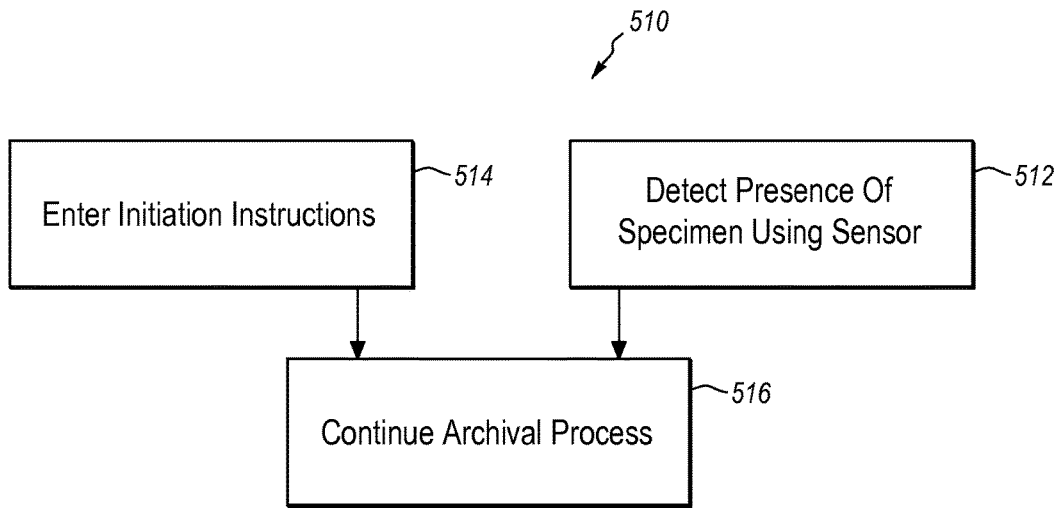
FIG. 6 illustrates an embodiment of a method for initiating the archival process according to the present invention.

FIG. 6 illustrates an embodiment of a method 510 for archival process initiation. In one embodiment, a user places a specimen having an information display (such as a UPC barcode, matrix barcode, QR code, or other information display, which may be associated with the specimen) in or on an input component or an input/output component, and the specimen archival process is initiated. In one embodiment, the input component or input/output component may include a sensor such as a weight sensor or a motion sensor that can sense when a specimen is positioned relative to the input component or input/output component. Upon sensing the specimen or specimens 512, the specimen archival process is initiated. In addition or alternatively, a user initiates the specimen archival process by entering instructions through the software program 514. Then, a number of automated steps performed by the system components may occur as the archival process continues 516.

Figure 7:
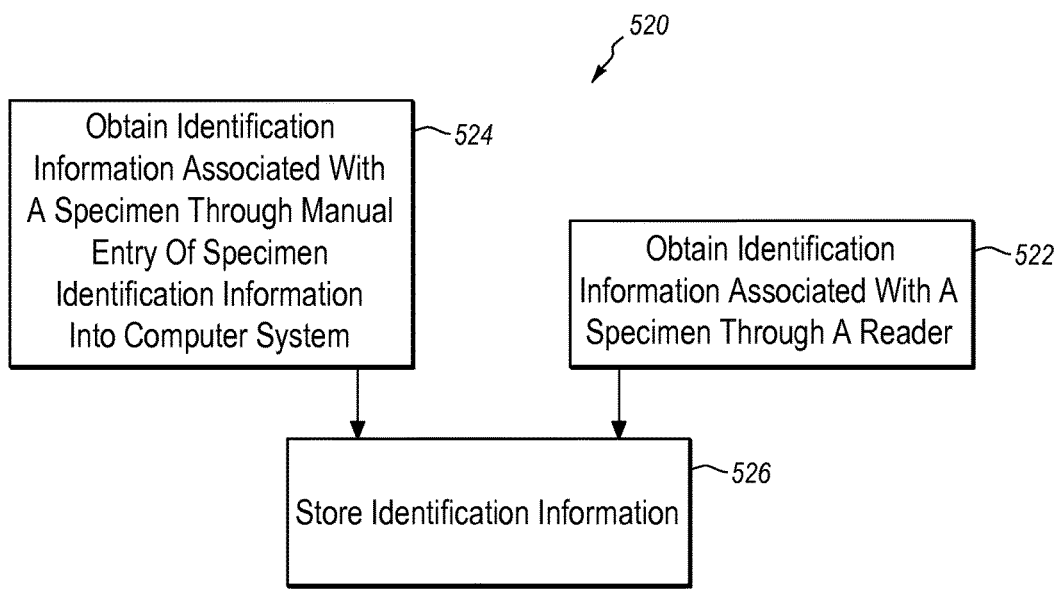
FIG. 7 illustrates an embodiment of a method for obtaining identification information associated with a specimen according to the present invention.

FIG. 7 illustrates an embodiment of a method 520 for obtaining identification information associated with a specimen. In one embodiment, a reader on the movement mechanism or other system component may read a specimen information display (such as a UPC barcode, matrix barcode, QR code, or other, which may be associated with the specimen) to ascertain specimen identification information 522. In addition or alternatively, the specimen identification information may be manually entered into the computer system 524. The information is sent to the software program, and is received and stored in the computer system 526.

Figure 8:
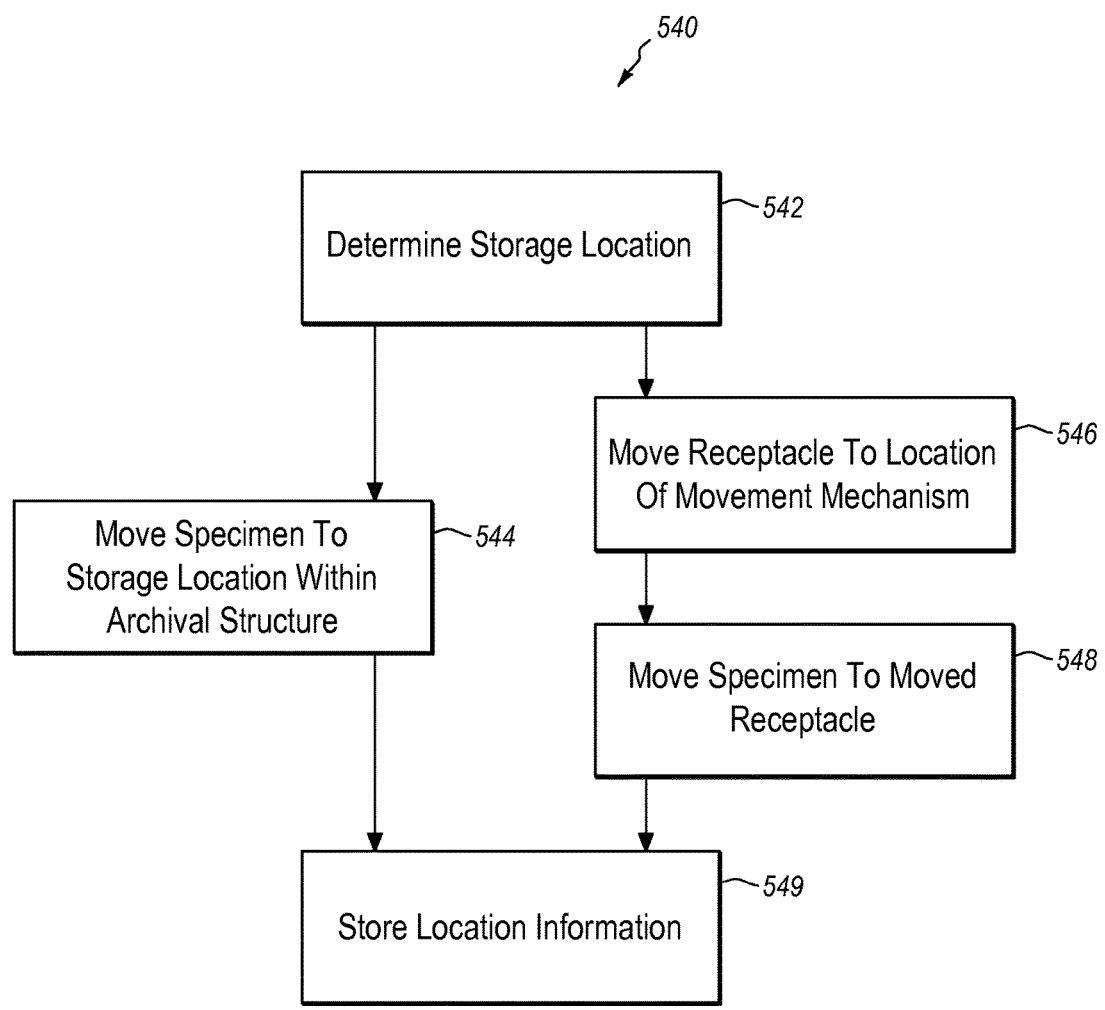
FIG. 8 illustrates an embodiment of a method for moving a specimen to a storage location according to the present invention.
Figure 9:
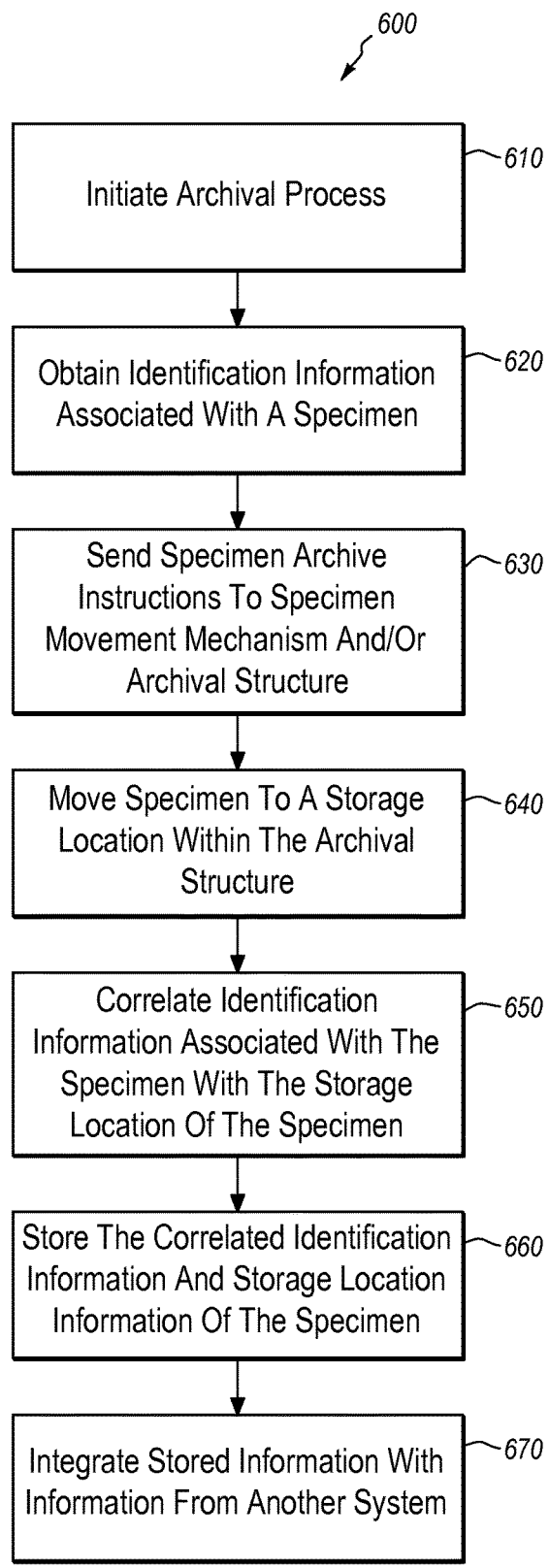
FIG. 9 illustrates an embodiment of a method for archiving specimens and integrating stored information with other systems according to the present invention.

FIG. 8 illustrates an embodiment of a method 540 for moving a specimen to a storage location within the archival structure. In one embodiment, the storage location is determined 542. In one embodiment, the storage location is determined according to the size of the specimen. In addition or alternatively, the storage location is determined according to the shape of the specimen. In addition or alternatively, the storage location is determined by the order the specimen is archived. In addition or alternatively, the storage location is determined according to user instructions. The specimen may be positioned 544 in a location within the archival structure or the receptacle may be moved 546 to the location of the movement mechanism and the specimen then moved 548 to the receptacle. The storage location of the specimen location may be sent to the to the software program and received and stored in the computer system 549. In any of the embodiments of the methods illustrated in FIGS. 5-8, certain steps may be repeated if additional specimens are to be archived. FIG. 9 illustrates another embodiment of a method 600 for an archival process.

The embodiment of FIG. 9 is similar to the embodiments of FIG. 5 and the description of FIG. 5 is incorporated herein by reference. In some embodiments, an archival process is initiated 610, identification information associated with a specimen is obtained 620, specimen archive instructions are sent 630, a specimen is moved to a storage location within the archival structure 640, identification information associated with the specimen is correlated 650 with storage location of the specimen, and the correlated identification and storage location information is stored 660. Additionally or alternatively, stored information regarding specimen identification and/or storage location may be integrated with information from another system 670. For example, the information may be integrated with information from other automated systems within the laboratory or other environment in which the system is implemented. For example, the information may be integrated with electronic medical records systems, digital microscopy, and/or digital scanning. It may also be integrated with other information in order to improve workflow, improve patient care because of reduced errors and delay in diagnosis, reduce cost due to increased efficiency, and improve morale. In some examples, the other system 670 may be located remotely (i.e. in a separate room, building, etc.) from the computer system (such as computer system 400). In other examples, the other system 670 may be located in the same general area (i.e. same floor, room, laboratory) as the computer system (such as computer system 400).

Figure 10:
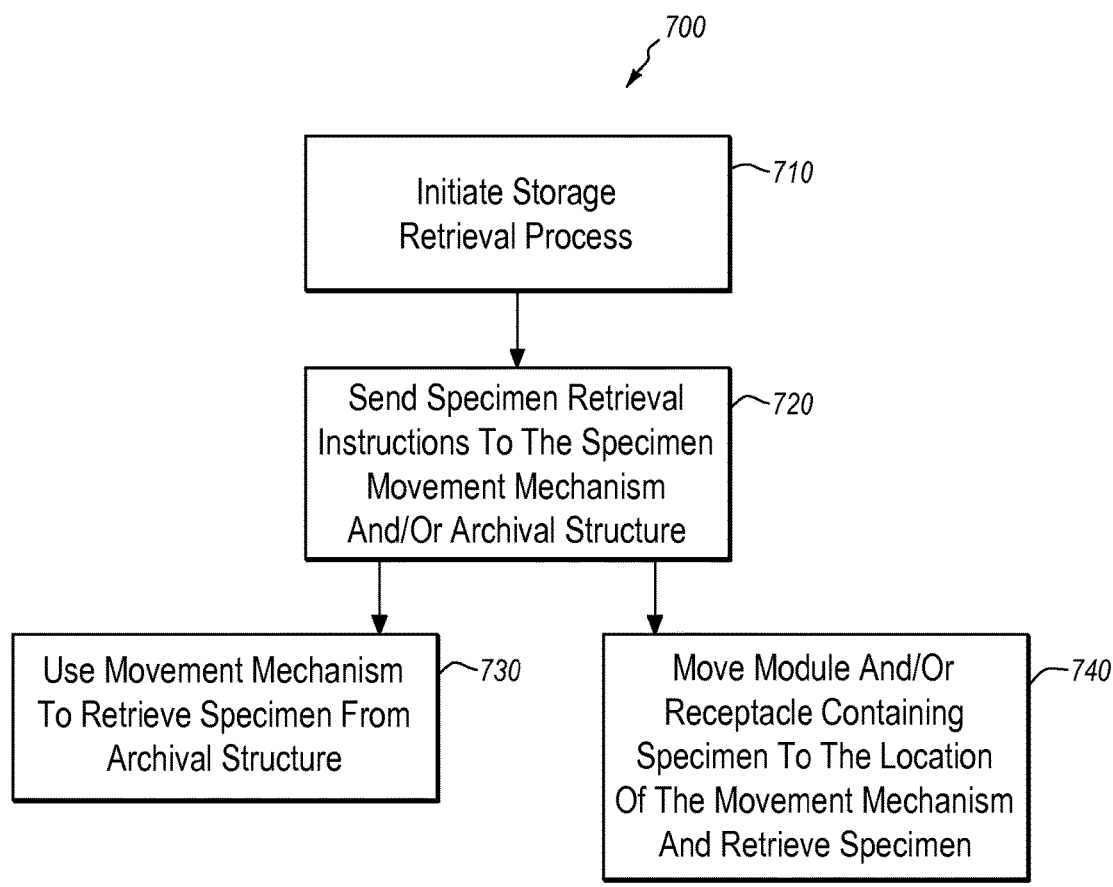
FIG. 10 illustrates an embodiment of a method for retrieving specimens according to the present invention.

FIG. 10 illustrates an embodiment of a method 700 for retrieval of a specimen. The retrieval of a specimen may be initiated 710 through the software program. The software program then transmits 720 a storage location to the movement mechanism and/or the archival structure, and the movement mechanism moves 730 to the location of the specimen or the specimen or the receptacle or module containing the specimen is moved 740 to the location of the movement mechanism.

Figure 11:
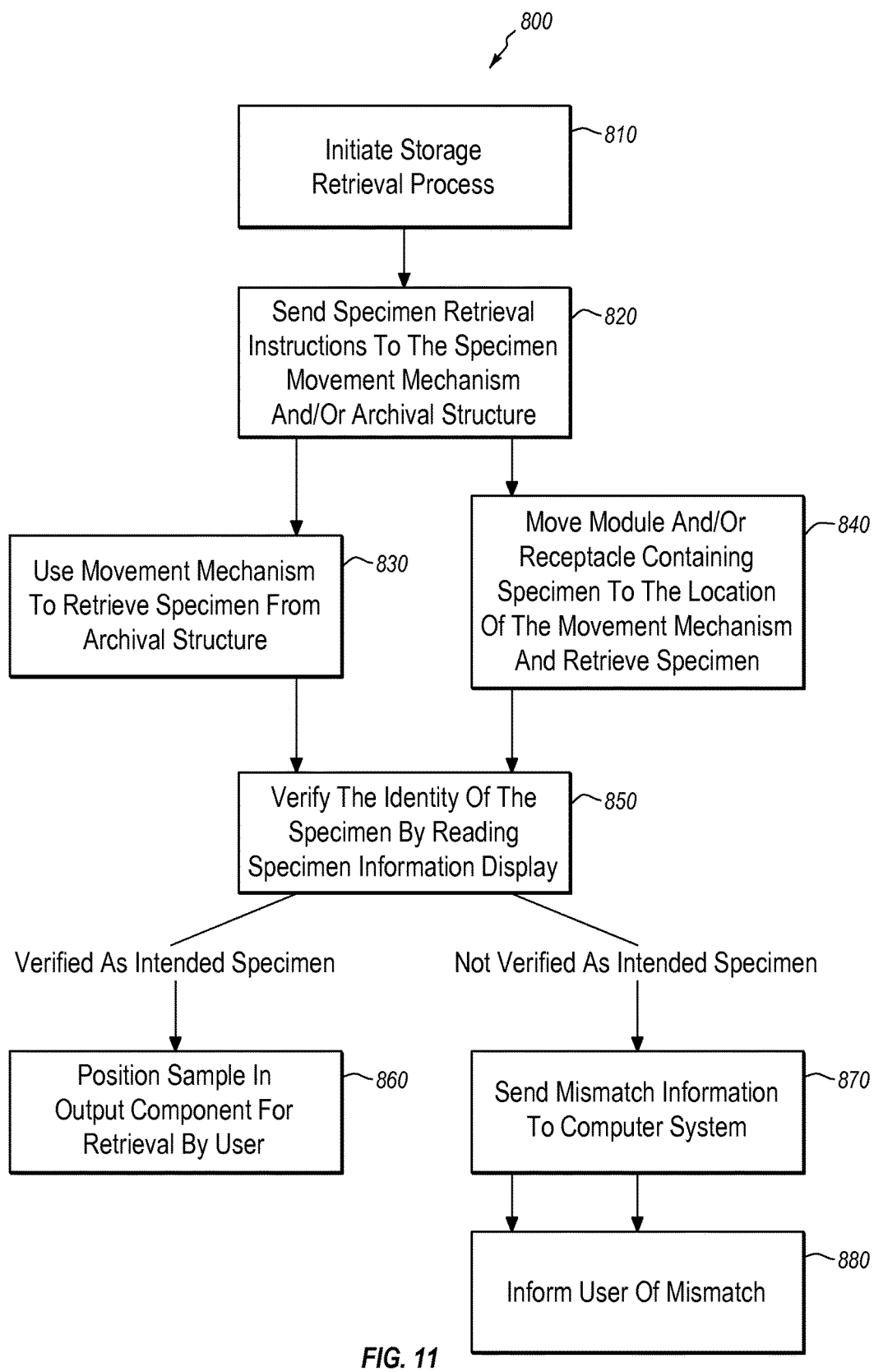
FIG. 11 illustrates an embodiment of a method for retrieving specimens and verifying the identity of specimens according to the present invention.

FIG. 11 illustrates another embodiment of a method 800 for retrieval of a specimen. The embodiments of FIG. 11 are similar to the embodiments of FIG. 10 and the description of FIG. 10 is herein incorporated by reference. In some embodiments, the storage retrieval process is initiated 810, specimen retrieval instructions are sent 820, and the movement mechanism moves 830 to the location of the specimen or the specimen or the receptacle or module containing the specimen is moved 840 to the location of the movement mechanism. Additionally, the identity of the retrieved specimen or specimens may be verified 850 by reviewing an information display (such as a UPC barcode, matrix barcode, QR code, or other, which may be associated with the specimen). The reviewing may be conducted by a human operator or a scanner such as an electronic scanner or an optical scanner. If the specimen is verified as the intended retrieval, the specimen is positioned 860 in the input/output component for retrieval by the user. If the specimen is determined to be a mismatch to the intended specimen, information is dispatched 870 regarding the mismatch to the computer system. A message informing the user of the mismatch is displayed 880. If mismatches are detected, the computer program may direct the scanner to rescan a section of specimens or even all stored specimens, and with the new information rebuild the information database.

Some embodiments include certain workflows according to the methods of the present invention. Specimens may be retrieved from the archival structure for digital scanning, and/or review by healthcare provider such as a pathologist or clinician and a patient. In some embodiments, there are a number of purposes for which the specimens may be retrieved from the archival structure. Such purposes include staining, slide assembly, slide review, image analysis, reporting results to patient, review for surgery, delivery, accession, grossing, processing, embedding, or microtomy.

The described embodiments are to be considered in all respects only as illustrative and not restrictive, and the scope of the present invention is not limited to the foregoing description. Those of skill in the art may recognize changes, substitutions, adaptations and other modifications that may nonetheless come within the scope of the present invention and range of the present invention.

What is claimed:

1. A system for archiving and retrieving specimens, comprising:
    an archival structure including an input location and an output location, wherein the input location is the same as the output location;
    at least one storage module, the at least one storage module including a plurality of receptacles configured for receiving and storing specimens, the receptacles including at least one support element;
    at least one specimen movement mechanism, wherein the specimen movement mechanism is configured to move a specimen from the input location to a storage location on one receptacle of the plurality of receptacles, wherein the specimen movement mechanism is a robotic arm;
    a receptacle positioning component configured to position the one receptacle of the plurality of receptacles to a location accessible by the specimen movement mechanism; and
    a software program, wherein the software program is configured to receive information regarding the storage location of the specimen and store the information on a computer readable storage medium of a computer system.

2. The system of claim 1, wherein the specimen movement mechanism includes a specimen reader, the specimen reader being configured to read a specimen information display located on the specimen and to send specimen information to the software program.

3. The system of claim 1, wherein the archival structure includes at least one input component located at the input location, and at least one output component located at the output location, the input component and the output component being configured to receive specimens for storage at the input location and receive specimens from storage and wherein the specimen movement mechanism, archival structure, and software program are configured to store specimens according to expected storage term, such that shorter storage term specimens are located at an area of the archival structure relatively closer to the input component or the output component and longer storage term specimens are located at an area of the archival structure relatively farther from the input component or the output component.

4. The method of claim 1, wherein each specimen requires a storage volume approximately 50% greater than the specimen volume.

5. The system of claim 1, wherein the software program includes a user interface, the user interface being configured to allow entry of specimen storage and retrieval instructions to be forwarded to the specimen movement mechanism and archival structure.

6. The system of claim 5, wherein the software program is further configured to receive information from the specimen movement mechanism and archival structure and display the information on the user interface.

7. The system of claim 6, wherein the computer system includes a communications interface configured to forward information from the software program to the specimen movement mechanism and archival structure and to forward information from the specimen movement mechanism and archival structure to the software program.

8. In a computer automated environment, a method of archiving and retrieving specimens, comprising:
    placing a specimen in an input location;
    initiating an archival process;
    obtaining identification information associated with a specimen;
    sending specimen archive instructions to a specimen movement mechanism;
    moving a receptacle of a plurality of receptacles to a location accessible by the specimen movement mechanism, the receptacles including at least one support element;
    moving the specimen from the input location to a storage location on the receptacle of the plurality of receptacles within an archival structure using the specimen movement mechanism, the archival structure including at least one storage module configured to store the plurality of receptacles;
    correlating the identification information associated with the specimen with the storage location of the specimen; and
    storing the correlated identification information and storage location information of the specimen on a computer readable storage medium of a computer system.

9. The method of claim 8, wherein obtaining identification information associated with a specimen comprises manual entry of the identification information by a user into the computer system.

10. The method of claim 8, further comprising:
    accessing the correlated identification information and storage location information of the specimen;
    sending specimen retrieval instructions to the specimen movement mechanism and/or archival structure; and
    retrieving the specimen from the archival structure using the specimen movement mechanism and delivering the specimen to an output location.

11. The method of claim 10, further comprising verifying the identity of the specimen by reading a specimen information display located on the specimen using a reader.

12. The method of claim 11, wherein the reader is located on the specimen movement mechanism.

13. The method of claim 11, further comprising sending match or mismatch information to the computer system and informing user of match or mismatch information.

14. A system for archiving and retrieving specimens, comprising:
    an archival structure including at least one storage module, the at least one storage module including a plurality of receptacles configured for receiving and storing specimens, the receptacles including at least one support element;

a specimen movement mechanism configured to move a specimen from an input location to a storage location on one receptacle of the plurality of receptacles, wherein the specimen movement mechanism is a robotic arm;

a receptacle positioning component configured to position the one receptacle of the plurality of receptacles to a location accessible by the specimen movement mechanism; and a software program configured to receive information regarding the storage location of the specimen and store the information on a computer readable storage medium of a computer system.

15. The system of claim 14, wherein the support elements are attached to a vertical receptacle positioning component and a horizontal receptacle positioning component configured to move a storage module or a moveable portion of the receptacles within the archival structure.

16. The system of claim 14, wherein the receptacle positioning component rotates in multiple orientations.

17. The system of claim 14, wherein the at least one support element supports a plate element and the plate element is configured such that a specimen may be positioned thereon.

18. The system of claim 14, wherein the receptacles have a volume of approximately 0.0005 to 0.000625 cubic feet each.

19. The system of claim 14, wherein the at least one support element supports the specimen directly.

20. The system of claim 19, wherein the plate element is removably attached to the at least one support element.

* * * * *